(12) United States Patent
Nakashima et al.

(10) Patent No.: US 12,347,544 B2
(45) Date of Patent: Jul. 1, 2025

(54) HEALTH PROMOTION SYSTEM AND HEALTH PROMOTION METHOD

(71) Applicant: TOYOTA JIDOSHA KABUSHIKI KAISHA, Toyota (JP)

(72) Inventors: Issei Nakashima, Katsushika-ku (JP); Toru Miyagawa, Seto (JP); Hideo Hasegawa, Nagoya (JP); Yusuke Kinoshita, Ota-ku (JP); Shotaro Yasuda, Taito-ku (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 132 days.

(21) Appl. No.: 18/336,726

(22) Filed: Jun. 16, 2023

(65) Prior Publication Data

US 2023/0410975 A1    Dec. 21, 2023

(30) Foreign Application Priority Data

Jun. 20, 2022   (JP) ................. 2022-098869

(51) Int. Cl.
*G16H 20/30*   (2018.01)
*A63B 24/00*   (2006.01)

(52) U.S. Cl.
CPC .......... *G16H 20/30* (2018.01); *A63B 24/0062* (2013.01); *A63B 2024/0068* (2013.01); *A63B 2230/755* (2013.01)

(58) Field of Classification Search
CPC ........ G16H 20/30; G16H 40/63; G16H 50/70; A63B 24/0062; A63B 2024/0068; A63B 2230/755; A63B 2024/0093; A63B 24/0087; A63B 24/0075; A63B 71/06; A63B 2225/15; A63B 2230/00; A63B 2230/015

See application file for complete search history.

(56) References Cited

U.S. PATENT DOCUMENTS

| 10,311,694 B2 * | 6/2019 | McIntosh ............... G06N 5/045 |
| 10,325,470 B2 * | 6/2019 | Ehlert ................. G08B 21/0461 |
| 12,042,688 B1 * | 7/2024 | Lewis-Dove ........ A63B 21/156 |

(Continued)

FOREIGN PATENT DOCUMENTS

| DE | 102006012959 A1 * | 9/2006 | ............ F25D 23/12 |
| JP | 2010-140119 A | 6/2010 | |
| JP | 2019-124012 A | 7/2019 | |

*Primary Examiner* — Sundhara M Ganesan
(74) *Attorney, Agent, or Firm* — Finnegan, Henderson, Farabow, Garrett and Dunner, LLP

(57) ABSTRACT

A first exemplary aspect is a health promotion system using a computer, the health promotion system including: a door mechanism configured to be opened by an operation performed by a person; a control unit configured to control the door mechanism; and identification information acquisition unit that acquires identification information for identifying the person who operates the door mechanism. The control unit acquires health condition information indicating a health condition of the person, determines whether or not the health condition satisfies a target value that is predetermined for the person identified by the identification information, and increases an exercise load of the operation for opening the door mechanism when the health condition does not satisfy the target value.

10 Claims, 3 Drawing Sheets

(56) References Cited

U.S. PATENT DOCUMENTS

| | | | |
|---|---|---|---|
| 2014/0155705 A1* | 6/2014 | Papadopoulos | A61B 5/1112 600/301 |
| 2019/0096218 A1* | 3/2019 | Ehlert | G08B 21/04 |
| 2021/0020069 A1* | 1/2021 | Komala | G01L 5/00 |
| 2021/0219875 A1* | 7/2021 | Milosevic | G16H 50/30 |
| 2023/0414992 A1* | 12/2023 | Spoo | A63B 22/0214 |

* cited by examiner

HEALTH PROMOTION SYSTEM AND HEALTH PROMOTION METHOD

CROSS REFERENCE TO RELATED APPLICATIONS

This application is based upon and claims the benefit of priority from Japanese patent application No. 2022-098869, filed on Jun. 20, 2022, the disclosure of which is incorporated herein in its entirety by reference.

BACKGROUND

The present disclosure relates to a health promotion system and a health promotion method.

Japanese Unexamined Patent Application Publication No. 2010-140119 discloses a system that determines a user's intention or state by analyzing physical information of the user, and causes a robot to perform a predetermined motion corresponding to the user's intention or state. According to the motion performed by the robot, a user voluntarily maintains the motor functions of the user and activates the mental and physical activities of the user, whereby care prevention is promoted.

SUMMARY

The system disclosed in Japanese Unexamined Patent Application Publication No. 2010-140119 does not significantly motivate a user to exercise, that is, it simply recommends exercise, and therefore the user may not exercise. That is, the system disclosed in Japanese Unexamined Patent Application Publication No. 2010-140119 has a problem that it is inferior in health promotion effect.

The present disclosure has been made in view of the above-described circumstances, and an object thereof is to provide a health promotion system and a health promotion method by which excellent health promotion effects can be obtained.

A first exemplary aspect is a health promotion system using a computer, the health promotion system including:
  a door mechanism configured to be opened by an operation performed by a person;
  a control unit configured to control the door mechanism; and
  identification information acquisition unit that acquires identification information for identifying the person who operates the door mechanism, in which
  the control unit acquires health condition information indicating a health condition of the person,
  the control unit determines whether or not the health condition satisfies a target value that is predetermined for the person identified by the identification information, and
  the control unit increases an exercise load of the operation for opening the door mechanism when the health condition does not satisfy the target value.

Another exemplary aspect is a health promotion method using a computer, the health promotion method including:
  acquiring identification information for identifying a person who operates a door mechanism;
  acquiring health condition information indicating a health condition of the person; and
  determining whether or not the health condition satisfies a target value that is predetermined for the person identified by the identification information,
  in which an exercise load of the operation for opening the door mechanism is increased when the health condition does not satisfy the target value.

As described above, in the exemplary aspect, health condition information indicating a health condition of a person who operates the door mechanism is acquired, it is determined whether or not the health condition satisfies a target value that is predetermined for the person, and when the health condition does not satisfy the target value, an exercise load of the operation for opening the door mechanism is increased. Therefore, excellent health promotion effects can be obtained by the exercise load of opening the door mechanism.

The health condition may be an amount of exercise, and when the amount of exercise is below the target value and hence does not satisfy the target value, the exercise load of the operation for opening the door mechanism may be increased.

The health condition may be a calorie intake, and when the calorie intake exceeds the target value and hence does not satisfy the target value, the exercise load of the operation for opening the door mechanism may be increased.

The health condition is a body weight, and when the body weight exceeds the target value and hence does not satisfy the target value, the exercise load of the operation for opening the door mechanism may be increased.

The person may be able to select not to change the exercise load, and when the person selects not to change the exercise load, a determination as to whether or not the health condition satisfies the target value may not be made and the exercise load may not be changed. In an emergency such as the occurrence of a disaster, the door mechanism can be quickly opened.

According to the present disclosure, it is possible to provide a health promotion system and a health promotion method by which excellent health promotion effects can be obtained.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Figure 1:
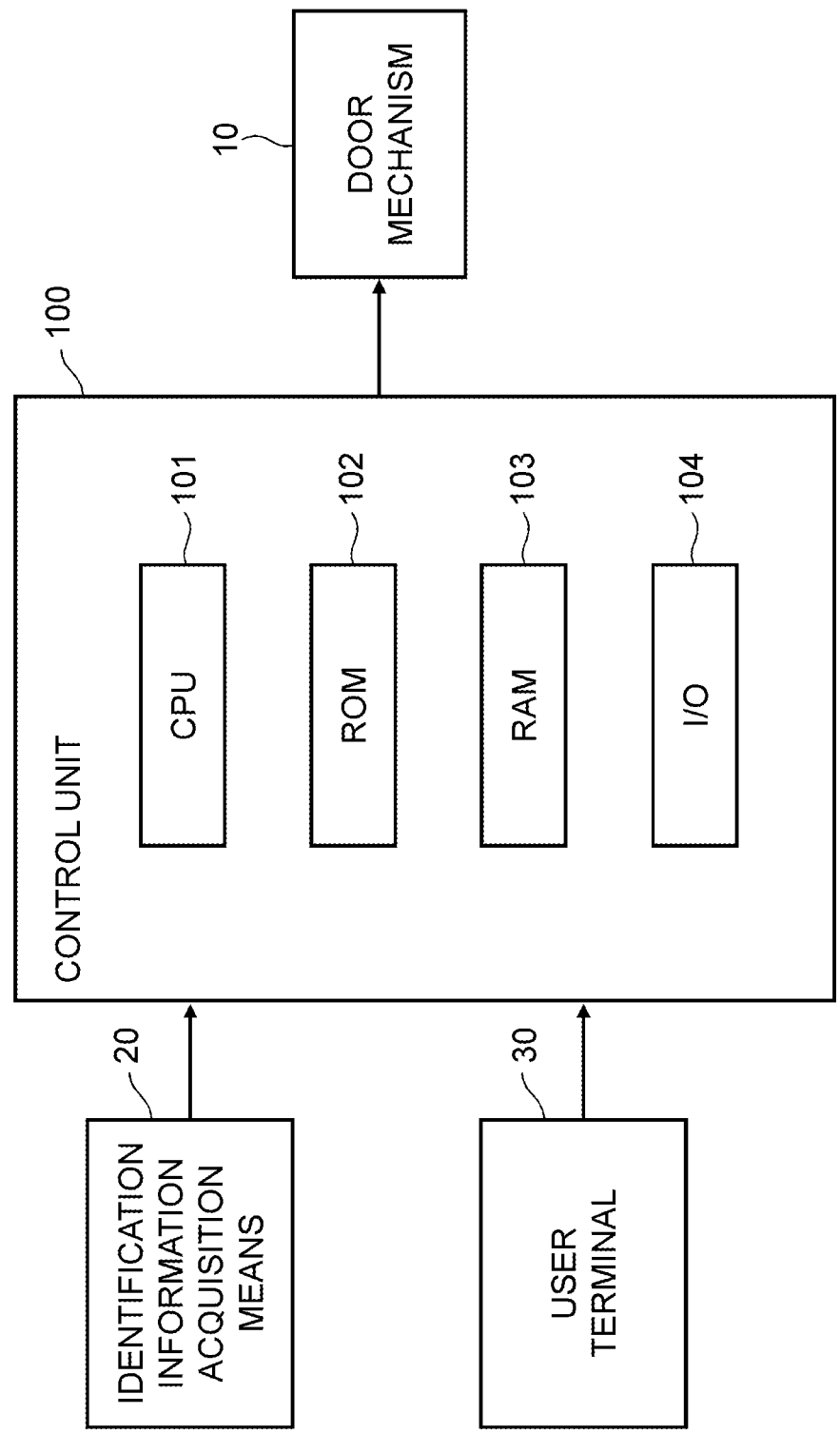
FIG. 1 is a block diagram showing a health promotion system according to a first embodiment.

Specific embodiments will be described hereinafter in detail with reference to the drawings. The same or corresponding elements are denoted by the same reference symbols throughout the drawings, and redundant descriptions will be omitted as necessary for the clarification of the description.

First Embodiment

<Configuration of Health Promotion System>

First, a health promotion system according to a first embodiment will be described with reference to FIG. 1. FIG.

1 is a block diagram showing the health promotion system according to the first embodiment. As shown in FIG. 1, the health promotion system according to this embodiment includes a door mechanism 10, identification information acquisition unit 20, a user terminal 30, and a control unit 100.

The door mechanism 10 is connected to the control unit 100, which is a computer, wirelessly or by wire, and is electronically controlled by the control unit 100 and opens in response to an operation performed by a person. The door mechanism 10 may be any door that is electronically controlled by the control unit 100 and opens in response to an operation performed by a person. For example, the door mechanism includes a lock mechanism which can be electronically controlled, and a locked state made by the lock mechanism is released in response to an operation performed by a person.

The identification information acquisition unit 20 is an electronic device which is connected to the control unit 100 wirelessly or by wire and which acquires identification information for identifying a person who operates the door mechanism 10. The identification information acquisition unit 20 is not limited to being specific means, and is, for example, a sensor, a camera, and the like for performing biometric authentication such as fingerprint authentication, vein authentication, iris authentication, and face authentication. Further, the identification information acquisition unit 20 may be, for example, a reader that reads an Integrated Circuit (IC) card for identity verification. Further, the identification information acquisition unit 20 may be, for example, an input device such as a touch panel or a keyboard for inputting a password and the like for identity verification.

The user terminal 30 is an electronic device which is connected to the control unit 100 wirelessly or by wire and which transmits health condition information indicating a health condition of a person who operates the door mechanism 10 to the control unit 100. The user terminal 30 is not limited to being a specific terminal, and is, for example, a mobile terminal such as a smartphone or a smartwatch carried by a person who operates the door mechanism 10.

Health condition information includes, for example, the amount of exercise (e.g., calories burned by exercise) for each day, a calorie intake through food etc. for each day, and a body weight for each day.

Note that the user terminal 30 may also serve as the identification information acquisition unit 20. For example, the identification information acquisition unit 20 may be a sensor, a camera, an input device, and the like mounted in the user terminal 30. Further, the user terminal 30 may be any electronic device that can transmit health condition information to the control unit 100. For example, instead of the user terminal 30, an input device such as a touch panel or a keyboard for a person who operates the door mechanism 10 to input health condition information may be connected to the control unit 100.

As shown in FIG. 1, the control unit 100 is connected to the door mechanism 10, the identification information acquisition unit 20, and the user terminal 30 wirelessly or by wire so that it can communicate with them.

As shown in FIG. 1, the control unit 100 includes, as hardware, a Central Processing Unit (CPU) 101, a Read Only Memory (ROM) 102, a Random Access Memory (RAM) 103, and an Input/Output (I/O) 104. That is, the control unit 100 has a function as a computer and performs various types of processing based on various types of control programs etc.

The CPU 101 is, for example, an arithmetic unit that performs control processing and arithmetic processing.

The ROM 102 is, for example, a storage unit that stores control programs and arithmetic programs executed by the CPU 101.

The RAM 103 is a storage unit that temporarily stores processing data and the like. In the RAM 103, for example, identification information of a person and a target value of a health condition of the person are associated with each other and stored.

The I/O 104 is an input and output device that inputs data and signals from the outside and outputs data and signals to the outside.

The control unit 100 controls the door mechanism 10 based on the identification information acquired by the identification information acquisition unit 20 and the health condition information received from the user terminal 30. More specifically, the control unit 100 determines whether the health condition satisfies a target value of the health condition that is predetermined for the person identified by the identification information acquired by the identification information acquisition unit 20.

Then, the control unit 100 increases the exercise load of an operation for opening the door mechanism 10 when the health condition does not satisfy the target value. For example, the control unit 100 increases the force required to rotate a door knob of the door mechanism 10, thereby increasing the exercise load of the operation. Alternatively, the control unit 100 sets the lock mechanism of the door mechanism 10 so that it is not released unless the door knob is rotated a plurality of times in order to open the door mechanism 10, thereby increasing the exercise load of the operation.

For example, when the health condition is an amount of exercise (e.g., calories burned by exercise) for each day and the amount of exercise is below a target value and hence does not satisfy the target value, the control unit 100 increases the exercise load of the operation for opening the door mechanism 10.

For example, when the health condition is a calorie intake through food etc. for each day, and the calorie intake exceeds a target value and hence does not satisfy the target value, the control unit 100 increases the exercise load of the operation for opening the door mechanism 10.

For example, when the health condition is a body weight for each day and the body weight exceeds a target value and hence does not satisfy the target value, the control unit 100 increases the exercise load of the operation for opening the door mechanism 10.

As described above, in the health promotion system according to this embodiment, it is determined whether or not the health condition of a person who operates the door mechanism 10 satisfies a target value of the health condition that is predetermined for the person. Then, when the health condition does not satisfy the target value, the exercise load of an operation for opening the door mechanism 10 is increased. Therefore, excellent health promotion effects can be obtained by the exercise load of opening the door mechanism 10.

<Health Promotion Method>

Figure 2:
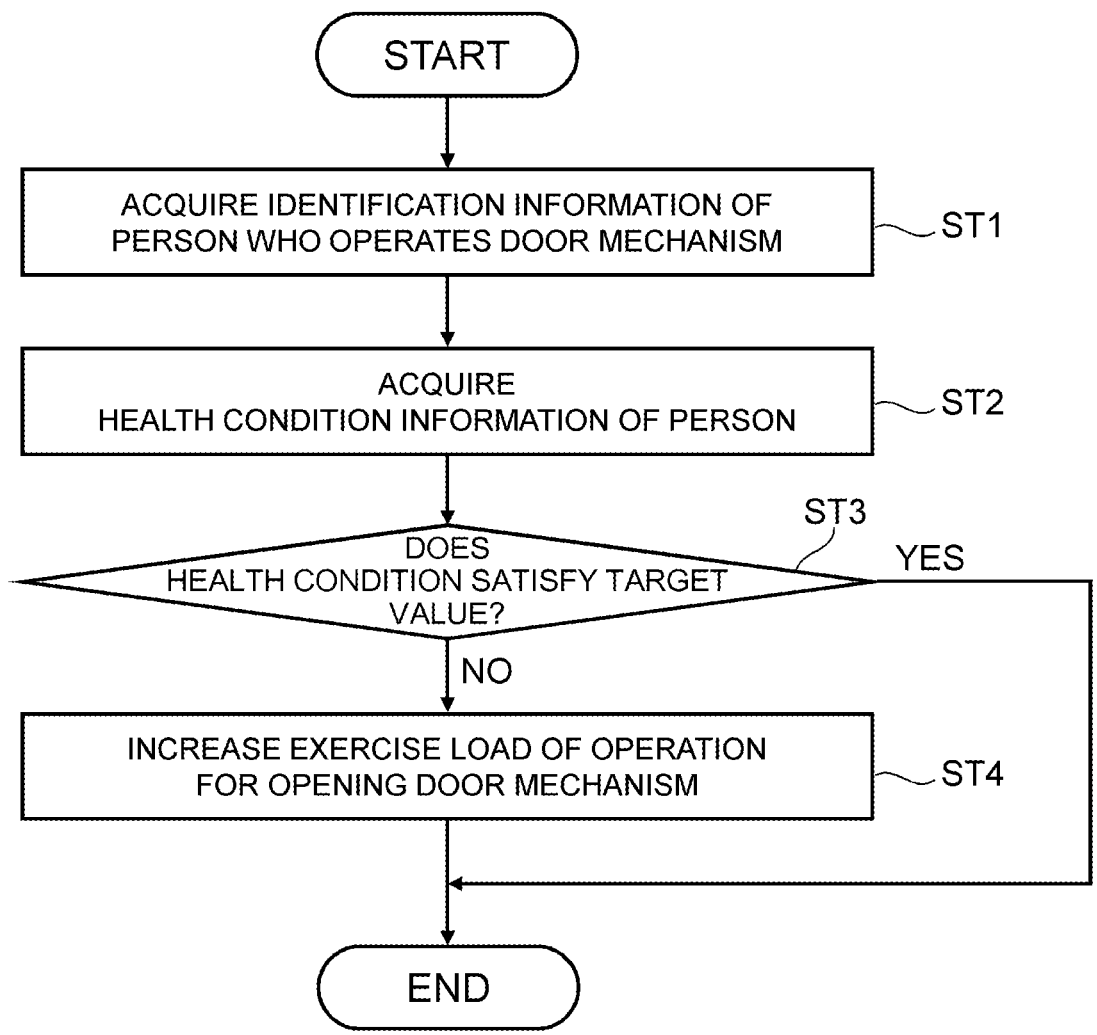
FIG. 2 is a flowchart showing a health promotion method according to the first embodiment.

Next, a health promotion method according to this embodiment will be described with reference to FIG. 2 as well as FIG. 1. FIG. 2 is a flowchart showing the health promotion method according to the first embodiment.

First, as shown in FIG. 2, the identification information acquisition unit 20 acquires identification information for identifying a person who operates the door mechanism 10

(Step ST1). Then the control unit 100 identifies the person based on the identification information acquired by the identification information acquisition unit 20.

Note that the identification information acquisition unit 20 may identify the person based on the acquired identification information.

Next, as shown in FIG. 2, the control unit 100 acquires health condition information of the person from the user terminal 30 (Step ST2).

Then, as shown in FIG. 2, it is determined whether or not the health condition of the person satisfies a target value of the health condition that is predetermined for the person (Step ST3). Note that the target value of the health condition of the person is associated with the identification information of the person and stored, for example, in a storage unit (e.g., the RAM 103 of the control unit 100 shown in FIG. 1).

When the health condition of the person satisfies the target value (YES in Step ST3), the control unit 100 does not change the exercise load of an operation for opening the door mechanism 10 and ends the control.

On the other hand, when the health condition of the person does not satisfy the target value (NO in Step ST3), the control unit 100 increases the exercise load of the operation for opening the door mechanism 10.

As described above, in the health promotion system according to this embodiment, it is determined whether or not the health condition of a person who operates the door mechanism 10 satisfies a target value of the health condition that is predetermined for the person. Then, when the health condition does not satisfy the target value, the exercise load of an operation for opening the door mechanism 10 is increased. Therefore, excellent health promotion effects can be obtained by the exercise load of opening the door mechanism 10.

Second Embodiment

Figure 3:
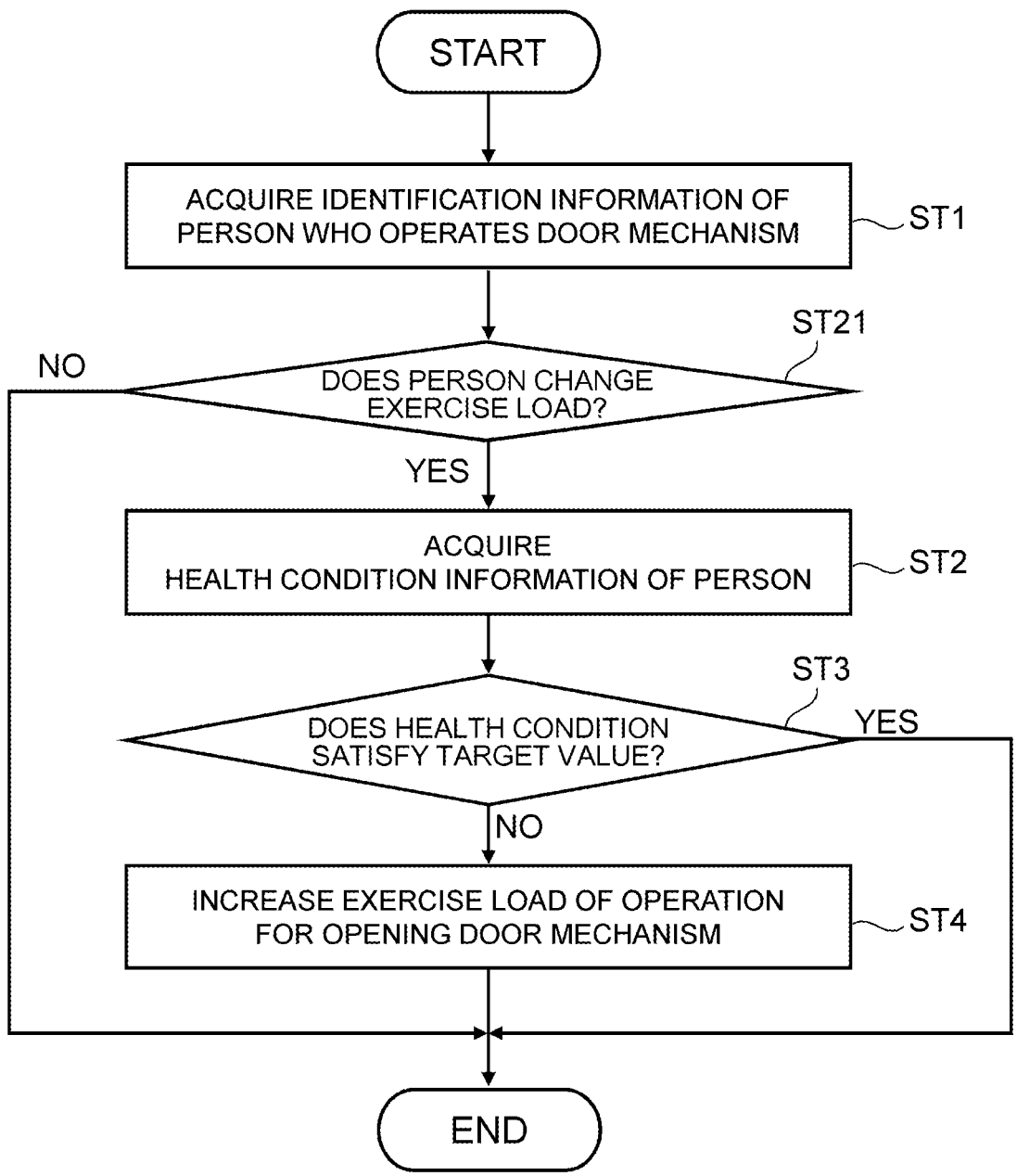
FIG. 3 is a flowchart showing a health promotion method according to a second embodiment.

Next, a health promotion system and a health promotion method according to the second embodiment will be described with reference to FIG. 3. FIG. 3 is a flowchart showing the health promotion method according to the second embodiment. Note that Steps ST1 to ST4 shown in FIG. 3 are the same as Steps ST1 to ST4 shown in FIG. 2.

In the health promotion system according to the second embodiment, it is possible to select whether to change the exercise load of an operation for opening the door mechanism 10.

Therefore, as shown in FIG. 3, after the identification information acquisition unit 20 acquires identification information for identifying a person who operates the door mechanism 10 (Step ST1), the person selects whether or not to change the exercise load of the operation for opening the door mechanism 10 (Step ST21).

When the person selects to change the exercise load of the operation for opening the door mechanism 10 (YES in Step ST21), the control unit 100 performs Steps ST2 to ST4 like in the case of FIG. 2.

On the other hand, when the person selects not to change the exercise load of the operation for opening the door mechanism 10 (NO in Step ST21), the control unit 100 does not change the exercise load of the operation for opening the door mechanism 10 and ends the control.

As described above, in the health promotion method according to this embodiment, it is possible to select whether to change the exercise load of an operation for opening the door mechanism 10.

Since a person usually selects to change the exercise load of the operation for opening the door mechanism 10, excellent health promotion effects can be obtained like in the health promotion method according to the first embodiment.

On the other hand, by not changing the exercise load of the operation for opening the door mechanism 10 in an emergency such as the occurrence of a disaster, the door mechanism 10 can be quickly opened under a normal exercise load.

The configurations other than the above ones are similar to those of the first embodiment, and the descriptions thereof will thus be omitted.

In the above example, the program includes instructions (or software codes) that, when loaded into a computer, cause the computer to perform one or more of the functions described in the example embodiments. The program may be stored in a non-transitory computer readable medium or a tangible storage medium. By way of example, and not a limitation, non-transitory computer readable media or tangible storage media can include a random-access memory (RAM), a read-only memory (ROM), a flash memory, a solid-state drive (SSD) or other types of memory technologies, a CD-ROM, a digital versatile disc (DVD), a Blu-ray (Registered Trademark) disc or other types of optical disc storage, and magnetic cassettes, magnetic tape, magnetic disk storage or other types of magnetic storage devices. The program may be transmitted on a transitory computer readable medium or a communication medium. By way of example, and not a limitation, transitory computer readable media or communication media can include electrical, optical, acoustical, or other forms of propagated signals.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A health promotion system using a computer, the health promotion system comprising:
   a door mechanism configured to be opened by rotation of a doorknob of the door mechanism, the rotation being performed by a person;
   a control unit configured to control the door mechanism; and
   identification information acquisition unit that acquires identification information for identifying the person who operates the door mechanism, wherein
   the door mechanism is electronically controlled by the control unit,
   the control unit acquires health condition information indicating a health condition of the person,
   the control unit determines whether or not the health condition satisfies a target value that is predetermined for the person identified by the identification information, and
   the control unit outputs a control signal to the door mechanism when the health condition does not satisfy the target value, the control signal causing an increase in an exercise load of an operation for opening the door mechanism by increasing a force required to rotate the doorknob of the door mechanism or increasing a number of turns of the doorknob required to open the door mechanism.

2. The health promotion system according to claim 1, wherein the health condition is an amount of exercise, and when the amount of exercise is below the target value and hence does not satisfy the target value, the exercise load of the operation for opening the door mechanism is increased.

3. The health promotion system according to claim 1, wherein the health condition is a calorie intake, and when the calorie intake exceeds the target value and hence does not satisfy the target value, the exercise load of the operation for opening the door mechanism is increased.

4. The health promotion system according to claim 1, wherein the health condition is a body weight, and when the body weight exceeds the target value and hence does not satisfy the target value, the exercise load of the operation for opening the door mechanism is increased.

5. The health promotion system according to claim 1, wherein the person is able to select not to change the exercise load, and when the person selects not to change the exercise load, the control unit does not determine whether or not the health condition satisfies the target value and does not change the exercise load.

6. A health promotion method using a computer, the health promotion method comprising:

acquiring identification information for identifying a person who operates a door mechanism, wherein the door mechanism is configured to be opened by rotation of a doorknob of the door mechanism by the person;

electronically controlling the door mechanism using the computer;

acquiring health condition information indicating a health condition of the person;

determining whether or not the health condition satisfies a target value that is predetermined for the person identified by the identification information; and outputting a control signal from the computer to the door mechanism when the health condition does not satisfy the target value, wherein the control signal causes an increase in an exercise load of an operation for opening the door mechanism by increasing a force required to rotate the doorknob of the door mechanism or increasing a number of turns of the doorknob required to open the door mechanism.

7. The health promotion method according to claim 6, wherein the health condition is an amount of exercise, and when the amount of exercise is below the target value and hence does not satisfy the target value, the exercise load of the operation for opening the door mechanism is increased.

8. The health promotion method according to claim 6, wherein the health condition is a calorie intake, and when the calorie intake exceeds the target value and hence does not satisfy the target value, the exercise load of the operation for opening the door mechanism is increased.

9. The health promotion method according to claim 6, wherein the health condition is a body weight, and when the body weight exceeds the target value and hence does not satisfy the target value, the exercise load of the operation for opening the door mechanism is increased.

10. The health promotion method according to claim 6, wherein the person is able to select not to change the exercise load, and when the person selects not to change the exercise load, a determination as to whether or not the health condition satisfies the target value is not made and the exercise load is not changed.

* * * * *